US010918354B2

(12) United States Patent
Nichol et al.

(10) Patent No.: US 10,918,354 B2
(45) Date of Patent: Feb. 16, 2021

(54) DEVICE AND METHOD FOR GUIDING CARDIOPULMONARY RESUSCITATION DURING CARDIAC ARREST

(71) Applicant: University of Washington, Seattle, WA (US)

(72) Inventors: Graham Nichol, Mercer Island, WA (US); Adeyinka Adedipe, Seattle, WA (US); Pierre D. Mourad, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 389 days.

(21) Appl. No.: 15/346,667

(22) Filed: Nov. 8, 2016

(65) Prior Publication Data
US 2017/0049413 A1  Feb. 23, 2017

Related U.S. Application Data

(63) Continuation of application No. PCT/US2015/032845, filed on May 28, 2015.
(Continued)

(51) Int. Cl.
*A61B 8/06*  (2006.01)
*A61B 8/08*  (2006.01)
*A61H 31/00*  (2006.01)
*A61B 8/04*  (2006.01)
*A61B 8/00*  (2006.01)

(52) U.S. Cl.
CPC ............... *A61B 8/065* (2013.01); *A61B 8/04* (2013.01); *A61B 8/06* (2013.01); *A61B 8/4281* (2013.01); *A61B 8/488* (2013.01); *A61H 31/005* (2013.01)

(58) Field of Classification Search
CPC ....... A61B 8/065; A61B 8/461; A61B 8/5223; A61B 8/4281; A61B 8/04; A61B 8/488;
(Continued)

(56) References Cited

U.S. PATENT DOCUMENTS 5,496,257 A * 3/1996 Kelly .................. A61H 31/005
600/454
5,701,898 A  12/1997 Adam et al.
(Continued)

FOREIGN PATENT DOCUMENTS

WO  2007/057825  5/2007
WO  2008042559  4/2008
(Continued)

OTHER PUBLICATIONS

PCT Application No. PCT/US2015/032845; International Search Report and Written Opinion dated Sep. 4, 2015; 10 pages.
(Continued)

*Primary Examiner* — Theodore J Stigell
*Assistant Examiner* — Johnathan Maynard
(74) *Attorney, Agent, or Firm* — Christensen O'Connor Johnson Kindness PLLC

(57) ABSTRACT

A medical device for providing guidance to administered cardiopulmonary resuscitation during cardiac arrest in a subject comprising a measuring probe to measure a hemodynamic property of blood flowing through a blood vessel of the subject, an interface element with reference indicia to guide the measuring probe to major blood vessels of the subject experiencing cardiac arrest, and a blood flow monitoring device comprising a data module to collect measured hemodynamic properties of the subject and a guidance module configured to display resuscitation guidance information for manipulating at least one hemodynamic property of the blood.

20 Claims, 6 Drawing Sheets

Related U.S. Application Data

(60) Provisional application No. 62/004,118, filed on May 28, 2014.

(58) Field of Classification Search
CPC ....... A61B 8/06; A61B 5/6822; A61B 5/7242; A61B 5/061; A61B 8/4236; A61B 5/0402; G09B 23/288; A61N 1/39; A61N 1/3925; A61H 31/00; A61H 31/004; A61H 31/005; A61H 31/006; A61H 31/007
See application file for complete search history.

(56) References Cited

U.S. PATENT DOCUMENTS

| | | | |
|---|---|---|---|
| 8,323,202 B2 | 12/2012 | Roschak et al. | |
| 8,600,496 B2 | 12/2013 | Kellum | |
| 2002/0133197 A1 | 9/2002 | Snyder et al. | |
| 2002/0173725 A1* | 11/2002 | Rock | A61B 8/4236 600/500 |
| 2004/0010180 A1 | 1/2004 | Scorvo | |
| 2004/0116969 A1* | 6/2004 | Owen | A61N 1/3625 607/6 |
| 2004/0267325 A1 | 12/2004 | Geheb et al. | |
| 2006/0241459 A1 | 10/2006 | Tai | |
| 2007/0060785 A1* | 3/2007 | Freeman | A61N 1/3625 600/16 |
| 2008/0015439 A1* | 1/2008 | Raju | G01S 15/58 600/455 |
| 2008/0228088 A1* | 9/2008 | Aubert | A61B 5/7282 600/485 |
| 2010/0022886 A1* | 1/2010 | Ayati | G09B 23/288 600/454 |
| 2011/0137173 A1 | 6/2011 | Lowe et al. | |
| 2011/0270089 A1 | 11/2011 | Vezina | |
| 2011/0301513 A1* | 12/2011 | Freeman | A61H 31/007 601/43 |
| 2012/0010543 A1* | 1/2012 | Johnson | A61H 31/00 601/41 |
| 2012/0016279 A1* | 1/2012 | Banville | A61H 31/004 601/41 |
| 2012/0184854 A1* | 7/2012 | Raju | A61B 8/4494 600/454 |
| 2013/0218057 A1* | 8/2013 | Jorgenson | A61N 1/3987 601/41 |
| 2013/0281897 A1* | 10/2013 | Hoffmann | A61B 8/0816 601/107 |
| 2013/0282069 A1* | 10/2013 | Thiagarajan | A61N 1/3993 607/3 |
| 2014/0039291 A1* | 2/2014 | Freeman | A61B 5/0295 600/380 |
| 2015/0265497 A1* | 9/2015 | Kaufman | A61H 31/006 601/41 |
| 2015/0283027 A1* | 10/2015 | Lampe | A61H 31/005 600/486 |
| 2016/0143805 A1* | 5/2016 | Aelen | A61B 5/021 601/41 |

FOREIGN PATENT DOCUMENTS

| | | |
|---|---|---|
| WO | 2012/117337 | 9/2012 |
| WO | 2014/066859 | 5/2014 |

OTHER PUBLICATIONS

Kim; Detection of Physiological Events by Impedance; Yonsei Medical Journal; 1989; 11 pgs; vol. 30; Issue 1.
Hightower et al.; Decay in Quality of Closed-Chest Compressions over Time; Annals of Emergency Medicine; Sep. 1995; pp. 300-303; vol. 26; Issue 3.
Ochoa et al.; The Effect of Rescuer Fatigue on the Quality of Chest Compressions; Resuscitation; 1998; pp. 149-152; vol. 37.
Aase et al.;. Compression Depth Estimation for CPR Quality Assessment Using DSP on Accelerometer Signals; IEEE Transactions on Biomedical Engineering; Mar. 2002; pp. 263-268; vol. 49; Issue 3.
Hallstrom et al.; Manual Chest Compression vs Use of an Automated Chest Compression Device during Resuscitation Following out-of-hospital Cardiac Arrest: a Randomized Trial; Journal of the American Medical Association; Jun. 14, 2006; pp. 2620-2628; vol. 295; Issue 22.
Abella et al.; CPR Quality Improvement during in-hospital Cardiac Arrest using a real-time Audiovisual Feedback System; Resuscitation; 2007; pp. 54-61; vol. 73.
Nichol et al.; Regional variation in out-of-hospital cardiac arrest incidence and outcome; Journal of the American Medical Association; Sep. 24, 2008; pp 1423-1431;vol. 300; Issue 12.
Neumar et al.; Post-Cardiac Arrest Syndrome; AMA Circulation; Dec. 2, 2008; pp. 2452-2483; vol. 118.
Perkins et al.; Compression Feedback Devices Over Estimate Chest Compression Depth when Performed on a Bed; Resuscitation; 2009; pp. 79-82; vol. 80.
Nishisaki et al.; Effect of Mattress Deflection on CPR Quality Assessment for Older Children and Adolescents; Resuscitation; 2009; pp. 540-545; vol. 80.
Nichol et al.; Regional Systems of Care for out-of-hospital Cardiac Arrest; American Heart Association Policy Statement; 2010; pp. 709-729; Circular 121.
Christenson et al.; Chest Compression Fraction Determines Survival in Patients with out-of-hospital Ventricular Fibrillation; AHA Circulation; Sep. 29, 2010; 17 pgs; vol. 120; Issue 13.
Peberdy et al.; Part 9: Post-Cardiac Arrest Care: 2010 American Heart Association Guidelines for Cardiopulmonary Resuscitation and Emergency Cardiovascular Care; AMA Circulation; Nov. 2, 2010; pp. S768-S786; vol. 122; Suppl 3.
Travers et al.; Part 4: CPR Overview: 2010 American Heart Association Guidelines for Cardiopulmonary Resuscitation and Emergency Cardiovascular Care; AHA Circulation; Nov. 2, 2010; pp. S676-S684; vol. 122; Suppl 3.
Fischer et al.; Effects and Limitations of an AED with Audiovisual Feedback for Cardiopulmonary Resuscitation: A Randomized Manikin Study; Resuscitation; 2011; pp. 902-907; vol. 82.
Dolgov et al., Detection of Chest Compression Depth with Intracorporeal Ultrasound Travel Time Measurement; 5th European IFMBE Conference; 2011; pp. 1031-1034; IFMBE Proceedings 37.
Hostler et al.; Effect of real-time Feedback during Cardiopulmonary Resuscitation Outside Hospital: Prospective, Cluster-randomised Trial; Biomedical Journal; Feb. 4, 2011; 10 pgs; vol. 342.
Leman; Audiovisual Feedback and Quality of CPR; Biomedical Journal; Feb. 4, 2011; 3 pgs; vol. 342.
Vaillancourt et al.; The Impact of Increased Chest Compression Fraction on Return of Spontaneous Circulation for out-of-hospital Cardiac Arrest Patients not in Ventricular Fibrillation; Resuscitation; Dec. 2011; pp. 1501-1507; vol. 82; Issue 12.
Gruber et al.; Real-Time Feedback Systems in CPR; Trends in Anaesthesia and Critical Care; 2012; pp. 287-294; vol. 2.
Stiell et al.; What is the Role of Chest Compression Depth during out-of-hospital Cardiac Arrest Resuscitation? Critical Care Medicine; 2012; pp. 1192-1198; vol. 40; Issue 4.
Idris et al.; The Relationship between Chest Compression Rates and Outcomes from Cardiac Arrest; AHA Circulation; Jun. 19, 2012; pp. 3004-3012; vol. 125; Issue 24.
Go et al.; Heart Disease and Stroke Statistics—2013 Update: A Report from the American Heart Association; AHA Circulation; Jan. 1, 2013; 489 pgs; vol. 127; Issue 1.
Bobrow et al.; The Influence of Scenario-based Training and real-time Audiovisual Feedback on out-of-hospital Cardiopulmonary Resuscitation Quality and Survival from out-of-hospital Cardiac Arrest; Annals of Emergency Medicine; Jul. 2013; pp. 47-56; vol. 62; Issue 1.
Adedipe et al.; To Push or Not to Push: Manual or Mechanical Compressions for Cardiac Arrest?; Critical Care Medicine; Jul. 2013; pp. 1824-1826; vol. 41; Issue 7.
Meaney et al.; Cardiopulmonary Resuscitation Quality: Improving Cardiac Resuscitation Outcomes Both Inside and Outside the Hos-

(56) References Cited

OTHER PUBLICATIONS pital, A Consensus Statement From the American Heart Association; AHA Circulation; Jul. 23, 2013; pp. 417-435; vol. 128.

Rubertsson et al.; Mechanical Chest Compressions and Simultaneous Defibrillation vs Conventional Cardiopulmonary Resuscitation in Out-of-Hospital Cardiac Arrest: The LNC Randomized Trial; The Journal of the American Medical Association; Nov. 17, 2013; pp. 53-61; vol. 311; Issue 1.

* cited by examiner

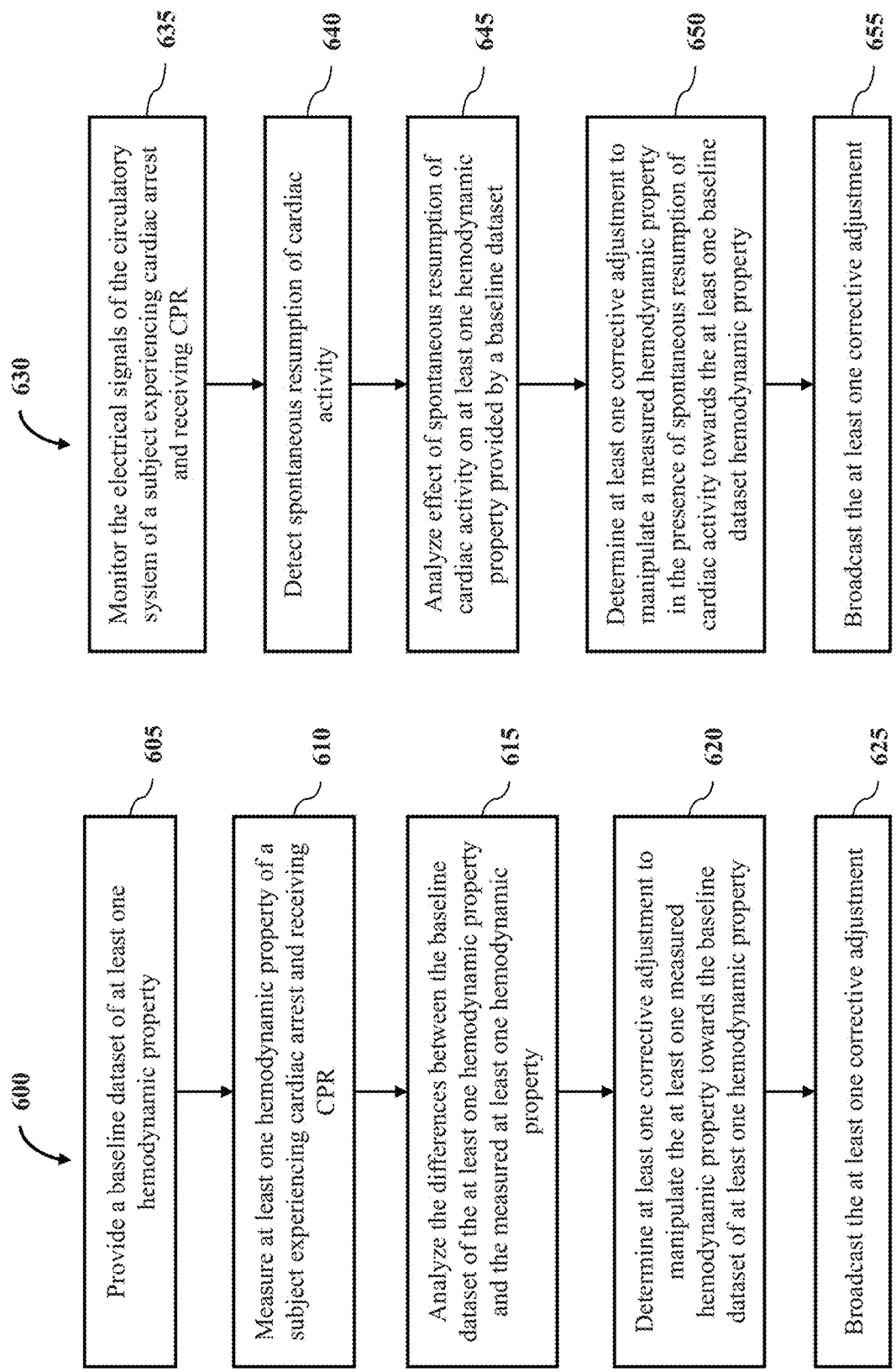

DEVICE AND METHOD FOR GUIDING CARDIOPULMONARY RESUSCITATION DURING CARDIAC ARREST

CROSS-REFERENCE TO RELATED APPLICATION

This application is a continuation of International Application No. PCT/US2015/0032845, filed May 28, 2015, which claims the benefit, under 35 U.S.C. § 119(e), of U.S. provisional patent application No. 62/004,118 filed May 28, 2014, entitled "Ultrasound Sensor in Cardiac Arrest" which are hereby incorporated by reference in their entirety.

BACKGROUND OF THE INVENTION

Cardiac arrest outside of medical facilities has a low survival rate and often imparts neurological deficits to many that do survive cardiac arrest. Effective administration of cardiopulmonary resuscitation (CPR) can improve survival rates and post-arrest conditions. Currently available CPR assistance tools to improve elements of CPR do not significantly increase survival rates. Accordingly, there is a need for systems and methods to beneficially modify administration of CPR in real time to increase survival rates and improve post-arrest conditions.

SUMMARY OF THE INVENTION

Devices, systems, and methods to provide real time feedback on the effectiveness of CPR and to broadcast corrective and prescriptive measures to improve the administration of CPR are described. Embodiments of the present invention relate to technologies that non-invasively measure the hemodynamic properties of a subject experiencing cardiac arrest. Hemodynamic properties are those that relate to the physical aspects of blood circulation. In one embodiment, the measured hemodynamic property is cardiac output through a carotid artery as measured by blood flow velocity. In another embodiment, the volume flow rate, or blood volume flux, through a blood vessel of the subject is measured. In other embodiments, blood pressure is the measured hemodynamic property, such as mean arterial pressure, systolic pressure, or diastolic pressure. In yet another embodiment, tissue properties directly associated with blood flow through a blood vessel are measured, such as pulsation of tissue at, or immediately adjacent to, the blood vessel. One of ordinary skill in the art can envision other hemodynamic properties beneficial for measurement and adjustment during the administration of CPR during cardiac arrest.

Embodiments of the present invention further analyze the pattern of the measured hemodynamic properties and compare the analysis to baseline patterns associated with optimal metrics. Optimal metrics may include hemodynamic properties associated with CPR resulting in subject survival, or hemodynamic properties of a healthy subject not experiencing cardiac arrest.

More specifically, embodiments of the present invention relate to devices, systems, and methods for directly measuring the hemodynamic properties of blood flowing to or from the head of a subject experiencing cardiac arrest and receiving CPR, and provides resuscitation guidance information. In one embodiment, the resuscitation guidance information prescribes corrective actions to the CPR to improve the quality of the measured hemodynamic property resulting in higher survival rates and enhanced post-arrest conditions of the subject. Though the following disclosure discusses particular embodiments of the invention treating cardiac arrest and the circulatory system, one of ordinary skill in the art will see applications of the present invention to other fluid manipulations related to other locations in the body and other organ systems.

Currently available devices and technologies are capable of indirectly measuring the blood flow velocity through the circulatory system of a subject suffering cardiac arrest by measuring light absorption in subcutaneous tissue associated with net tissue perfusion. These tools are capable of determining if a state of cardiac arrest is present; they do not provide specific prescriptive feedback for improving directly measured blood flow by adjusting CPR administered to a cardiac arrest subject or provide objective analysis on the quality of blood flow so measured. Such devices merely provide information without context for the relevance of the information.

Other currently available devices attempt to replicate manual CPR with an automated compression device, or measure the chest compression depth during administration of CPR. These devices use chest compression as a proxy or indirect measure for blood flow. Such devices address the American Heart Association's compression components of CPR but do not measure any hemodynamic variable or significantly improve actual survival rates. Further, these devices fail to account for subjective factors related to the subject (for example, body composition, vascular condition, age, or pre-existing loss of blood) and treat all CPR recipients similarly. These universal response devices promote delivering a common solution to CPR, without recognizing that blood flow or other hemodynamic properties differ according to subjective factors, and do not measure the actual effectiveness of chest compressions in moving blood through the circulatory system. These devices further do not account for spontaneous resumption of cardiac functions during CPR, or whether spontaneous resumption is sufficient to maintain necessary coronary or cerebral perfusion to improve survival rates or post-resuscitation conditions.

Analyzing hemodynamic properties in the large blood vessels of a subject receiving CPR to provide resuscitation guidance information, such as by corrective adjustments to administration of chest compressions in accordance with treatment algorithms associated with cardiac arrest survival, solves the shortcomings of the current art. Embodiments of the present invention provide a direct measure of hemodynamic properties incident to CPR. Direct measures of blood flow provide accurate information related to coronary and cerebral perfusion, enabling precise prescriptive adjustments to improve the administration of CPR for surviving cardiac arrest or mitigating post-arrest conditions.

Merely by way of example of providing CPR guidance, an embodiment measures blood flow velocity by applying an ultrasonic transducer to the carotid artery of a subject experiencing cardiac arrest and receiving CPR. In one embodiment, the transducer is guided to the artery by an interface element with reference indicia aligning to anatomical references. Certain embodiments include medical adhesive to hold the transducer in the correct location overlying an artery throughout a diagnosis or treatment period. In another embodiment, the interface element is applied to the subject with a hydrogel to enhance the propagation of acoustic signals to and from the artery. In another embodiment, the transducer transmits the measured blood flow velocity to a blood flow monitoring device. In one embodiment, the blood flow monitoring device receives the measured blood flow velocity in a data module. In another embodiment, the blood flow monitoring device further comprises a guidance module. In one embodiment, the guidance module displays resuscitation guidance information, such as corrective adjustments to the administered CPR or a display of measured hemodynamic properties. In another embodiment, the guidance module stores a baseline dataset of optimal blood flow measures and analyzes the differences between the blood flow measured by the transducer and the optimal blood flow velocity of the baseline dataset, and provides corrective adjustments to manipulate the measured blood flow velocity towards the optimal blood flow velocity. In another embodiment, the transducer has multiple sensors configured to detect bidirectional flow (such as flow to the brain in an artery and also flow away from the brain in a vein. These measures can be recorded by the data module and analyzed to calculate net flow or perfusion to the brain.

In another illustrative embodiment, an electrocardiogram node detecting any spontaneous resumption of cardiac activity is coupled to the blood flow monitoring device. The blood flow monitoring device detects cardiac activity from the electrocardiogram node and provides adjustments to CPR to maintain optimal blood flow velocity in the presence of any detected cardiac activity as compared to optimal blood flow velocity provided by a baseline dataset.

Another illustrative embodiment of the present invention is a method of providing resuscitation guidance during cardiac arrest of a subject receiving CPR. In one embodiment, merely as an example, the method begins by measuring the blood flow velocity through an arterial line of the patient. In one embodiment, a baseline dataset of blood flow velocity through an arterial line is provided as a reference point for optimized blood flow. In other embodiments, the differences between the measured blood flow velocity and the baseline dataset is calculated. In one embodiment, at least one corrective adjustment to CPR administered, or to be administered, to the subject is determined to conform the measured blood flow velocity to the baseline dataset. Many corrective adjustments are of course possible and are further discussed throughout this disclosure, though one of ordinary skill in the art will readily appreciate the many possibilities enabled by embodiments of the present invention. In one embodiment, the corrective adjustment is broadcast, such as by audio command.

These and other embodiments of the invention along with many of its advantages and features are described in more detail in conjunction with the text below and attached figures.

BRIEF DESCRIPTION OF THE DRAWINGS

The foregoing aspects and many of the attendant advantages of this invention and its embodiments will become more readily apparent when the accompanying detailed description is taken in conjunction with the following figures.

FIG. 6A-B illustrates processes for providing resuscitation guidance during cardiac arrest by providing a baseline dataset of hemodynamic properties, measuring the hemodynamic properties of a patient experiencing cardiac arrest, analyzing the differences between the baseline dataset and the measured properties, detecting spontaneous resumption of cardiac activity of a subject, determining a corrective adjustment to cardiopulmonary resuscitation, and broadcasting the corrective adjustment according to an embodiment of the present invention;

DETAILED DESCRIPTION OF THE INVENTION

Figure 1:
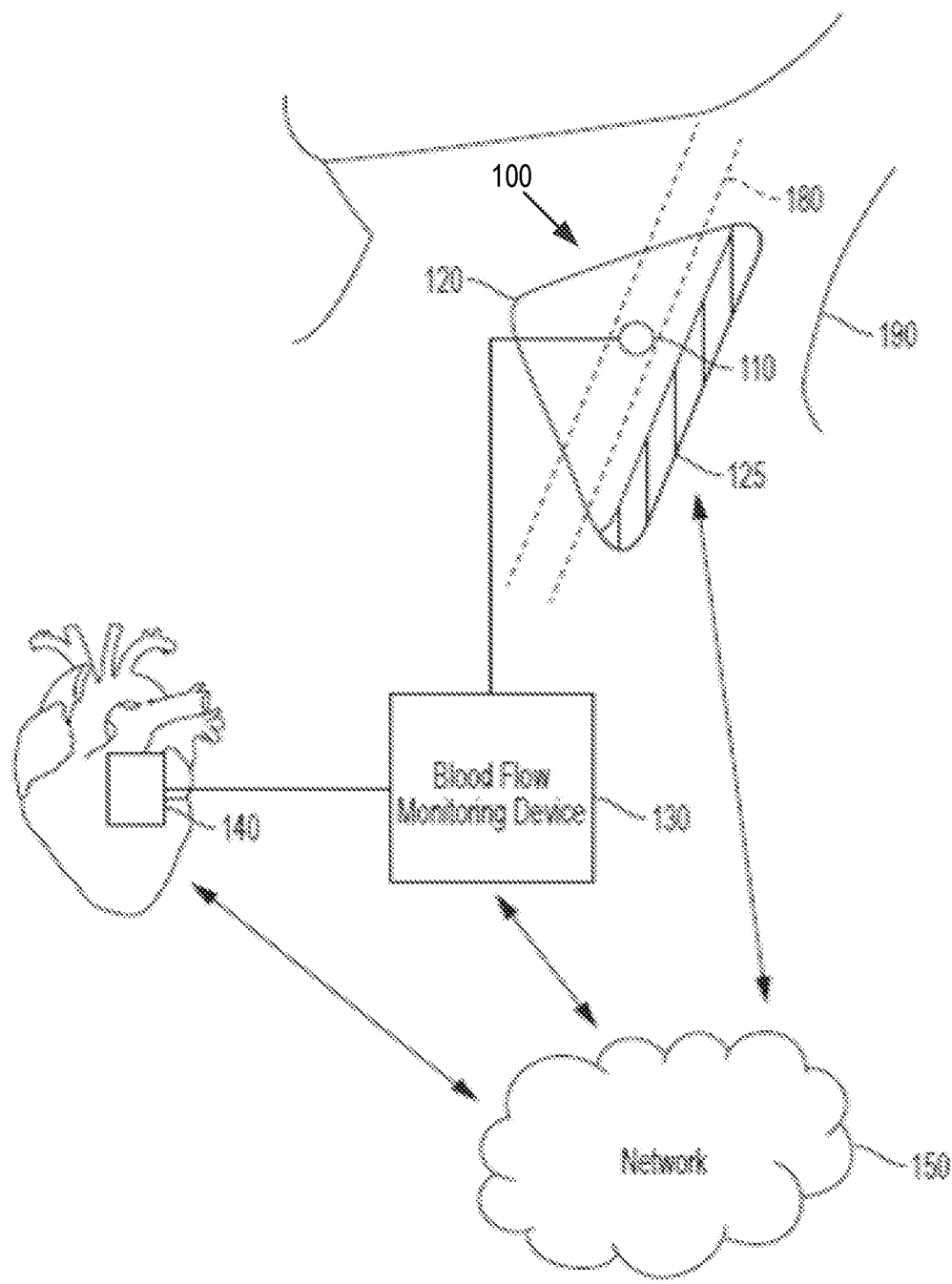
FIG. 1 illustrates a resuscitation guidance device comprising a measuring probe, an interface element with reference indicia, an electrical depolarization probe, and a blood flow monitoring device according to an embodiment of the present invention.

Embodiments of the present invention relate to technologies to provide real time guidance to CPR administered to a subject experiencing cardiac arrest. In one embodiment of a resuscitation guidance device, a measuring probe measures at least one hemodynamic property in a blood vessel of a subject experiencing cardiac arrest and receiving CPR. In one embodiment, the measuring probe is a directional probe that measures a hemodynamic property of blood flowing towards the head of the subject. In another embodiment, the measuring probe is bidirectional or has multiple sensors that measure the hemodynamic properties of blood flowing towards and away from the head of the subject. In one embodiment, the measuring probe is an ultrasonic transducer and measures at least one hemodynamic property by the Doppler effect. In another embodiment, at least one hemodynamic property is measured by infrared spectroscopy through the skin into a blood vessel of the subject; such infrared spectroscopy compares the photons of the blood cells received from an infrared transducer to create laser-based Doppler. In still other embodiments, the measuring probe is a listening device that does not transmit sound in a Doppler relation, but measures received sound signals of blood in the subject's blood vessel only. Other embodiments measure the mechanical pulsation of tissue proximate to the blood vessel, such as measuring by a polyvinylidine flouride (PVDF) transducer or other hydrophone or transducer-based system.

In one embodiment, the measuring probe measures the hemodynamic properties of blood flowing to the head of a subject experiencing cardiac arrest. Other embodiments measure the hemodynamic properties of blood flowing from the head of the subject. In still other embodiments, both flow of blood towards and from the head of the subject is measured to provide a measure of net hemodynamic properties, such as cerebral perfusion, to the head of the subject.

In one embodiment, blood flow velocity is at least one measured hemodynamic property. In another embodiment, volume flow rate of blood, or blood volume flux, is at least one measured hemodynamic property. Volume flow rate is measured by determining the velocity of blood calculated by the measuring probe, such as by the Doppler equation, and integrating across the cross sectional area of the vessel. The cross sectional area of the vessel in one embodiment is an estimated vessel area from biological references or other proxy; the cross sectional area of the vessel in other embodiments is determined by the measuring probe itself according to techniques well known in the art. Other hemodynamic properties measured in other embodiments include velocity of blood through the vessel. In one embodiment, blood pressure such as mean arterial pressure, or systolic and diastolic pressure is the at least one measured hemodynamic property. In another embodiment, blood vessel dilation is the at least one hemodynamic property measured by the measuring probe. In another embodiment, tissue pulsation proximate to a blood vessel is the at least one measured hemodynamic property.

In one embodiment the blood vessel the measuring probe measures hemodynamic properties within is a carotid artery. In other embodiments, the femoral artery is the blood vessel measured by the measuring probe. Other embodiments measure hemodynamic properties through other major blood vessels such as the brachial artery or temporal vessels or veins such as the jugular vein of a subject.

In one embodiment, the measuring probe has a face configured for application to the subject. In one embodiment, the face of the measuring probe is positioned at an angle to enable propagation of measuring signals to or from the measuring probe in parallel, or near parallel, with blood vessels. In other embodiments, the face of the measuring probe is configured for signals to or from the measuring probe to transmit perpendicular to a blood vessel of the subject. In one embodiment, the angle of the measuring probe face is predetermined, such as by mechanical fixtures, to standoff at a certain angle for every measuring probe. In another embodiment, the angle of the measuring probe face is adjustable and during application may be positioned or manipulated during resuscitation to enhance recording of measuring signals.

Some embodiments include an interface element to guide the measuring probe to an appropriate blood vessel. In one embodiment, the interface is operably coupled to the measuring probe to provide a medium between the subject and the measuring probe. In one embodiment, the interface element comprises structures to angle the measuring probe when coupled with the interface element to transmit or receive signals from or to the measuring probe in parallel, or near parallel, with a blood vessel of a subject. Such structures may be grooves or ridges on the interface element where the measuring probe is coupled.

In one embodiment, the interface element has reference indicia to align the interface element with a blood vessel such that when the measuring probe is coupled with the interface element, the measuring probe is proximate to the vessel. In other embodiments, the signals of the measuring probe are calibrated to detect blood flow through the vessel independent of proximity to the vessel. Reference indicia in one embodiment are visual cues, such as a straight edge with indicators to align the straight edge with the sternocleidomastoid muscle system of the subject or the anterior triangle of the neck to place the interface element over the carotid artery. In other embodiments, reference indicia are arrows on the interface element pointing to anatomical references of the subject such as the laryngeal prominence or jaw line such that aligning the arrows with the anatomical references places the interface element over the target blood vessel. In still other embodiments, the reference indicia textually describe the correct position of the interface element. In other embodiments, anatomical references not associated with the carotid artery guide placement, such as by aligning the interface element by guiding reference indicia to the inguinal ligament to place the interface element overlying or anterior to the femoral artery.

In one embodiment, a side of the interface element comprises an adhesive material to affix the interface element to the subject. In another embodiment, the interface element includes an attachment for securing the transducer to the interface element. In such embodiments, the transducer and interface elements do not require manually securing or maintaining the resuscitation guidance device to the subject throughout resuscitation. In one embodiment, the adhesive comprises hydrogel material, such as medical grade hydrogel, to improve propagation of signals from the measuring probe through the subject to a blood vessel. In one embodiment, the hydrogel is arranged on the interface element in variable layers and orientations to angle signals to or from the measuring probe in parallel, or near parallel, with a blood vessel of a subject.

One embodiment includes a blood flow monitoring device operably coupled to the measuring probe. The blood flow monitoring device contains various modules and components according to various embodiments.

In one embodiment, a data module of the blood flow monitoring device collects at least one hemodynamic property measured by the measuring probe. The data module, in one embodiment, analyzes the collected at least one hemodynamic property and creates a waveform over time of the measured at least one hemodynamic property. In another embodiment, a waveform created by the data module comprises changes in the pattern of the measured at least one hemodynamic property. In one embodiment, a guidance module coupled to the blood flow monitoring device displays resuscitation guidance information by presenting the waveform of the at least one measured hemodynamic property. An experienced health care provider can observe the displayed waveform and make autonomous corrective adjustments to administered CPR to improve the measured hemodynamic property to survival rate thresholds.

In certain embodiments, the resuscitation guidance device includes an electrical depolarization probe, such as an electrocardiogram node, to detect spontaneous cardiac activity during cardiac arrest. Certain embodiments of a blood flow monitoring device include an electrical signal detection module to receive any cardiac activity signals from the electrical depolarization probe.

In another embodiment, the blood flow monitoring device includes a database of baseline datasets associated with various hemodynamic properties. Hemodynamic properties stored in the database of baseline datasets may include the minimum hemodynamic properties of resuscitation historically demonstrative of survival or mitigation of post-arrest conditions, or the hemodynamic properties of healthy subjects not experiencing cardiac arrest. Specific hemodynamic properties include, but are not exhaustive of, blood flow velocity, volume flow rate, blood pressure, or tissue dilation. Many other datasets may be included as baseline datasets in the database; for example, in one embodiment the Reynolds number of laminar blood flow is stored in the database, or hemodynamic properties associated with subjective factors such as age or other physiological factors is stored in the database. Merely by way of example, if the subject suffering cardiac arrest were a two hundred pound sixty year old male, the baseline dataset could provide hemodynamic properties of similar subjects. One of ordinary skill in the art could envision further hemodynamic properties located in a database of baseline datasets.

In another embodiment, the guidance module provides direct resuscitation guidance information. According to one embodiment, the resuscitation guidance occurs in real time. In one embodiment, the guidance module of the blood flow monitoring device compares the metrics of at least one measured hemodynamic property as collected by the data module to a baseline dataset of an associated hemodynamic property as provided by the database. For example, if the measured at least one hemodynamic property is blood flow velocity the associated baseline dataset provided the guidance module by the baseline dataset database is also blood flow velocity. In one embodiment, differences between the at least one measured hemodynamic property and the associated hemodynamic property of the baseline dataset are calculated. In other embodiments, a CPR corrective adjustment is determined to manipulate the administration of CPR and manipulate measured hemodynamic properties towards the baseline dataset in accordance with the calculated difference.

In another embodiment, the corrective adjustment is forwarded to an output module of the blood flow monitoring device. In one embodiment, the output module displays the corrective adjustment calculated by the guidance module. Display in one embodiment is on a graphic user interface, such as by textual command or prompt; in another embodiment the display is by audio command. In yet another embodiment, the display is to a third party. In other embodiments, the output module forwards the at least one measured hemodynamic property, the baseline dataset of an associated hemodynamic property, or the corrective adjustment to an external source. External sources may include a third party observer, or a records database specific to the subject experiencing cardiac arrest and receiving CPR, or in one embodiment to a resuscitation delivery machine such as a chest compression device. Similarly, in other embodiments the measuring probe or the data module transmits at least one measured hemodynamic property to a third party through the output module in addition to transmitting to the blood flow monitoring device or guidance module.

Merely by way of example of calculating a corrective adjustment, in one embodiment the amplitude peaks of the measured blood flow velocity of blood as measured by the measuring probe and collected by the data module of the blood flow monitoring device are further apart than the amplitude peaks of the blood flow velocity of the baseline dataset; embodiments of the guidance module and blood flow monitoring device respond by displaying a command to increase chest compression rate; other embodiments display a command to increase the depth of chest compressions. In another illustrative example, the amplitudes of the peaks of the measured blood flow velocity are less than the peaks of the blood flow velocity of the baseline dataset; embodiments of the guidance module and blood flow monitoring device respond by issuing a command to increase the depth of the chest compressions. In another embodiment, the electrical signal detection module detects spontaneous resumption of cardiac activity during resuscitation. The guidance module compares the strength of the spontaneous cardiac activity with the baseline dataset; in one embodiment, if the spontaneous cardiac activity provides sufficient hemodynamic properties consistent with survival rates of cardiac arrest, the blood flow monitoring device displays a command to cease CPR on the output module or guidance module.

In another embodiment, the guidance module calculates the Reynolds number of the measured blood flow as a function of velocity of the blood as measured by the measuring probe. Reynolds numbers under 2300 are associated with laminar blood flow and Reynolds numbers over 4000 are associated with turbulent blood flow. For measurements indicating turbulent blood flow, the guidance module issues a command to adjust the CPR to reduce the velocity of the blood to produce laminar flow within the vessel. Other calculated adjustments in accordance with other fluid dynamic properties are of course possible and one of ordinary skill in the art will readily appreciate the many possibilities enabled by embodiments of the present invention.

In yet another embodiment, the blood flow monitoring device includes a storage module. The storage module, according to various embodiments, can cache the measured hemodynamic properties during the subject's cardiac arrest episode, or the calculated adjustments as determined by the guidance module. The storage module can later be accessed by higher or follow on care personnel. The cached information can lead to follow on prescriptive treatment taking the cached information into account. Additionally, cached information that resulted in survival and mitigated post-arrest conditions can be relayed to the baseline dataset database to update the information located there with additional baseline datasets associated with successful CPR administration.

In another embodiment the blood flow monitoring device further comprises a processor. In one embodiment, the processor contains computer readable instructions to execute transmission and reception of measuring probe signals to detect at least one hemodynamic property within a blood vessel of a subject experiencing cardiac arrest and receiving CPR, such as the blood flow velocity in an artery. In another embodiment, the processor contains instructions to convert the received signals into a waveform representing the at least one measured hemodynamic property or changes to the at least one measured hemodynamic property over time. In another embodiment, the processor contains instructions to access a baseline dataset of hemodynamic properties associated with survival in cardiac arrest or mitigation of post-arrest conditions of the subject. In still another embodiment, the processor contains instructions to compare the waveform of received signals of at least one measured hemodynamic property to the hemodynamic property of the baseline dataset, and further embodiments of the processor contain instructions to calculate differences between the two and determine a corrective adjustment to administered CPR to conform the received at least one measured hemodynamic property with the hemodynamic property of the baseline dataset. Still other embodiments include a processor with instructions to display the corrective adjustment to the CPR. Other embodiments include a processor with instructions to relay the at least one measured hemodynamic property to an external source, such as a medical record of the subject or a medical professional, in real time. Other embodiments include a processor with instructions for storing the at least one measured hemodynamic property, or waveform of the least one measured hemodynamic property, on a storage module for future access.

Communication between the various components of the resuscitation guidance device is enabled in various ways according to embodiments of the invention. In one embodiment, wired connections between the components transmit the associated information. In another embodiment, a network system (such as the internet, near field communication, or other wireless systems) enables communication. The communication methods enabled by such wireless systems permit third party or other external sources to provide real time baseline datasets in addition to those stored in the baseline dataset database. For example, a remote health care provider can monitor the state of cardiac arrest and observe the resulting hemodynamic properties and provide CPR instructions in lieu of or in addition to the guidance module resuscitation guidance information according to various embodiments.

Though the components are described and illustrated in the figures, and as more fully described below in reference to the figures, as being located with a common system, various embodiments of the invention distribute the components across several platforms. For example, in one embodiment, the blood flow monitoring device is located on a mobile device (such as a smart phone or tablet) independent of direct connection to the measuring probe or electrocardiogram node. In other embodiments, the modules and components of the blood flow monitoring device itself are distributed across several platforms.

Another embodiment of the present invention is a method to improve CPR by providing guidance to concurrently applied CPR on a subject experiencing cardiac arrest. In one embodiment, at least one hemodynamic property is measured in the subject. In one embodiment the measurement is by a single element transducer. In another embodiment, measurement is by a multi-element transducer, such as an imaging transducer. Transducers may vary according to embodiment, and include but are not limited to ultrasonic transducers, infrared spectroscopy, PVDF, or hydrophone. The at least one measured hemodynamic property in one embodiment is velocity of blood through a vessel, and in other various embodiments is volume flow rate or blood pressure. In one embodiment, the at least one measured hemodynamic property is collected as a waveform over time of the collected property to provide changes to the at least one hemodynamic property over time.

In another embodiment, the method includes a step to provide a baseline dataset of at least one hemodynamic property associated with the at least one measured hemodynamic property. The baseline dataset in one embodiment is a globally desired target of the at least one hemodynamic property, but in other embodiments is a subjective target of hemodynamic properties such as those for subjects of a certain age or suffering certain conditions. Subjects of a certain age, or that have suffered blood loss incident to the cardiac arrest, will have various desired targets of hemodynamic properties.

In one embodiment, at least one corrective adjustment to CPR administered to the cardiac arrest subject is determined. The corrective adjustment is determined by comparing the at least one measured hemodynamic property of the subject with an associated hemodynamic property of the baseline dataset, much in the same way as explained elsewhere in this disclosure. As previously described, the corrective adjustment can be to increase the frequency or depth of chest compressions for measured hemodynamic properties with amplitude waves less frequent as compared to the frequency of amplitude waves of the associated hemodynamic property of the baseline dataset. In other embodiments the distance between the peak and valley of the resulting waveform of the at least one measured hemodynamic property is compared to the peak and valley difference of the associated hemodynamic property of the baseline dataset; the corrective adjustment can be to increase chest compression depth or to permit increased chest recoil subsequent to compression accordingly. In still other embodiments, the corrective adjustment increases the area under the curve of waveform created from the measured at least one hemodynamic property by either increasing the amplitude of the measured at least one hemodynamic property or increasing the frequency of amplitudes for hemodynamic properties that cannot have the amplitudes increased (such as for physiological reasons).

In some embodiments, the corrective adjustment is broadcast. The specific means of broadcast varies according to the embodiment. In one embodiment, the broadcast is through a visual display on a graphic user interface, in another embodiment the broadcast is by audio command. One of ordinary skill in the art can envision many other broadcasting methods.

In another embodiment, the method includes a step to monitor the electrical depolarization signals of the circulatory system of the subject experiencing cardiac arrest. In the event the heart of the subject spontaneously resumes cardiac activity, the strength of the resultant activity and its effect on a hemodynamic property is analyzed against an associated hemodynamic property of a baseline dataset. If the spontaneous activity is strong enough, independent of CPR, to support hemodynamic properties consistent with survival of cardiac arrest as compared to the baseline dataset, a corrective adjustment to cease CPR is determined and broadcast. In the event the spontaneous activity is not strong enough to independently maintain the baseline dataset hemodynamic property, additional CPR adjustments to maintain the desired property in conjunction with the spontaneous cardiac activity are broadcast.

In another embodiment, hemodynamic properties measured throughout the administration of CPR are stored. Storage of the properties permits subsequent analysis of the hemodynamic properties present during, and resultant from, CPR; follow on care can then reference the stored measurements to make more informed decisions about subject treatment. Additionally, measured properties that led to survival or mitigation of post-arrest conditions are updated, in other embodiments, for future provision to baseline datasets to allow subsequent methods for guiding CPR to reference the more expansive corpus of successful hemodynamic properties during administration of CPR.

Turning now to the figures, FIG. 1 illustrates a resuscitation guidance device 100 applied to a subject 190 experiencing cardiac arrest and receiving CPR. Resuscitation guidance device 100 comprises a measuring probe 110 coupled to an interface element 120. In one embodiment, measuring probe 110 is an imaging or non-imaging ultrasonic transducer. In another embodiment, measuring probe 110 is an infrared spectrometer, though many alternatives exist and are further described in this disclosure. In one embodiment, measuring probe 110 measures at least one hemodynamic property of subject 190, such as blood flow velocity of the blood of subject 190; in other embodiments, measuring probe 110 measures blood pressure of subject 190 and in still other embodiments, measuring probe 110 measures the velocity of the blood of subject 190. In another embodiment, measuring probe 110 is directional and measures blood flowing through a vessel towards the head of subject 190, such as carotid artery 180. In still another embodiment, measuring probe 110 is bidirectional and measures blood flowing through vessels towards and away from the head of subject 190, such as carotid artery 180 and a jugular vein (not shown).

In one embodiment, interface element 120 guides measuring probe 110 to a blood vessel with reference indicia 125. In one embodiment, reference indicia 125 is an edge of the interface element 120 configured to align with an anatomical reference of subject 190. Suitable anatomical references vary according to embodiments of the invention. In one embodiment, the anatomical reference is a mandibular muscle of subject 190 to align reference indicia 125 and place interface element 120 over carotid artery 180. In another embodiment (not shown) the anatomical reference is the inguinal ligament of subject 190 to align reference indicia 125 and place interface element 120 over a femoral artery. In such embodiments, reference indicia 125 is an anatomical landmark to align with the anatomical reference. In other embodiments, reference indicia 125 is a visual cue, such as a graphic or textual explanation, for where to affix interface element 120. For example, in one embodiment reference indicia 125 are arrows pointing to anatomical references like the sternocleidomastoid muscle group or laryngeal prominence of subject 190 such that aligning the arrows with the indicated anatomical reference places interface element 120 over the desired blood vessel such as carotid artery 180. In other embodiments, reference indicia 125 is a specific textual instruction for placing interface element 120 on subject 190, such as "Align this edge with the sternocleidomastoid" or "Place this corner where the ear meets the neck."

In one embodiment, interface element 120 comprises material for propagating signals from measuring probe 110 to and from subject 190. In another embodiment, interface element 120 comprises an adhesive (not shown) to affix interface element 120 to subject 190, permitting continued application of interface element 120 to subject 190 during CPR without sustained manual application. In another embodiment, the adhesive further comprises a hydrogel, such as medical grade hydrogel, to further enhance propagation of signals to and from subject 190 with measuring probe 110.

In another embodiment, resuscitation guidance device 100 comprises a blood flow monitoring device 130. Blood flow monitoring device 130 is configured to collect measurements of at least one hemodynamic property from measuring probe 110. Further capabilities of blood flow monitoring device 130 are further explained below in conjunction with FIG. 2.

In another embodiment, resuscitation guidance device 100 comprises electrical depolarization probe 140 affixed on the surface of subject 190 in proximity to the heart. In one embodiment, electrical depolarization probe 140 is an electrocardiogram node, but in other embodiments is a suitable probe for detecting cardiac activity such as spontaneous resumption of circulatory functions such as a pulse or heartbeat detection probe. In one embodiment, electrical depolarization probe 140 is coupled to blood flow monitoring device 130 to provide electrical signals of the circulatory system of subject 190.

In one embodiment of resuscitation guidance device 100, measuring probe 110 and interface element 120 are a common component, such that the functions of both components as described above are performed by a single structure. In other embodiments of resuscitation guidance device 100, measuring probe 110, blood flow monitoring device 130 and electrical depolarization probe 140 are connected through a wired system. In another embodiment of resuscitation guidance device 100, measuring probe 110, blood flow monitoring device 130 and electrical depolarization probe 140 are connected through network 150 enabling wireless communication between the various components. Network 150 in one embodiment is a wireless network such as the internet, local area network, or near field communication; one of ordinary skill in the art will envision other suitable network connections for the components of resuscitation guidance device 100, and such network connection alternatives and means are not essential to understanding the present invention.

Figure 2:
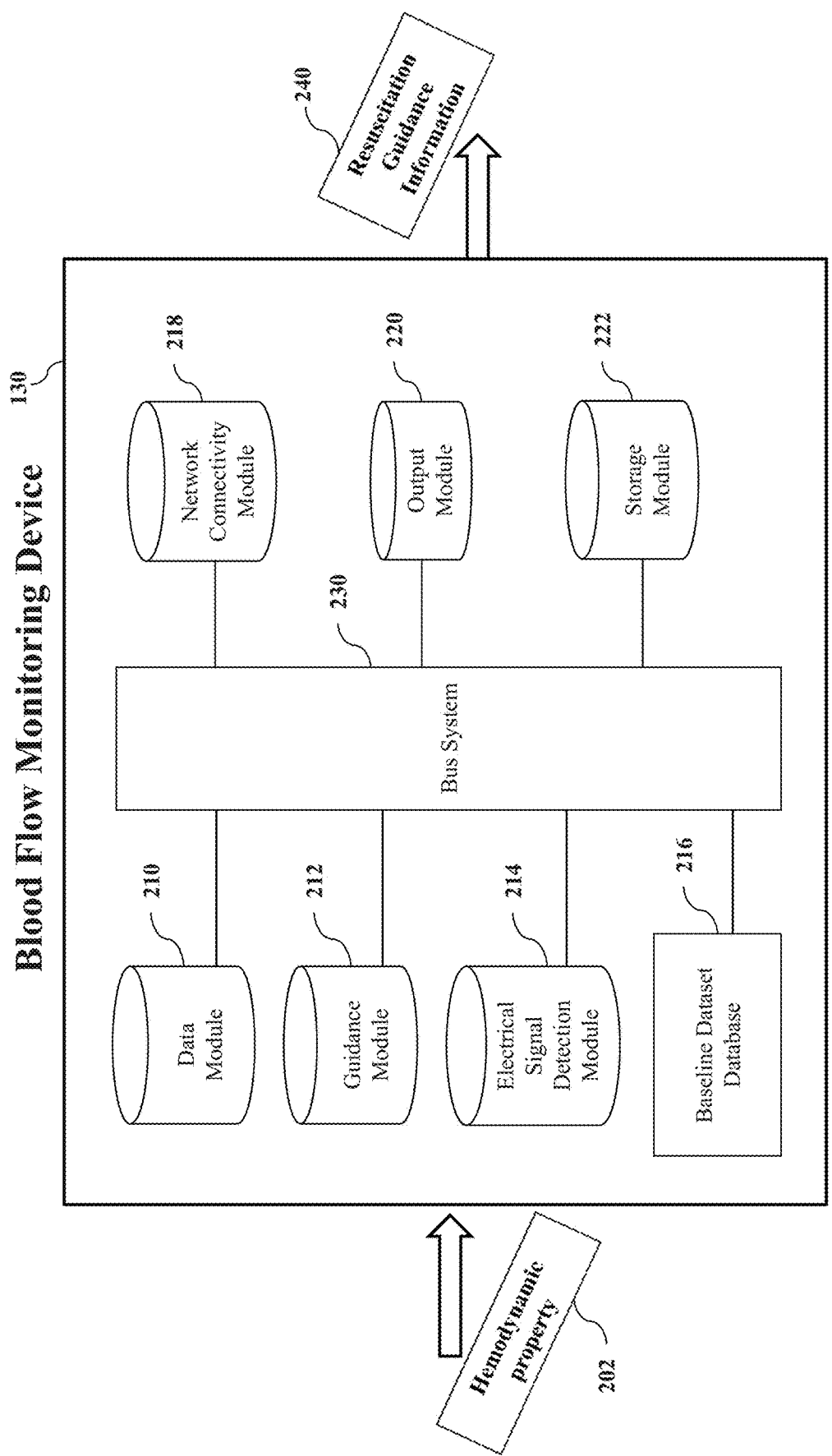
FIG. 2 illustrates a system diagram of a blood flow monitoring device comprising a data module, a guidance module, an electrical signal detection module, a baseline dataset database, a network connectivity module, an output module and a storage module all connected by a bus system and configured to receive a hemodynamic property, and produce resuscitation guidance information according to an embodiment of the present invention.

FIG. 2 illustrates embodiments of a blood flow monitoring device 130 in fuller detail. In one embodiment, blood flow monitoring device 130 comprises a data module 210 to collect at least one hemodynamic property 202 of a subject experiencing cardiac arrest and receiving CPR. Data module 210 can further be configured to transform the measured at least one hemodynamic property 202 to a waveform over time of the at least one hemodynamic property 202. In another embodiment, blood flow monitoring device 130 comprises guidance module 212. Guidance module 212 is coupled to data module 210 in one embodiment, and is configured to display at least one resuscitation guidance information 240 to manipulate CPR and adjust the at least one hemodynamic property 202.

In another embodiment, blood flow monitoring device 130 comprises a baseline dataset database 216. Baseline dataset database 216 contains various hemodynamic properties according to embodiments of the invention. Baseline hemodynamic properties in the baseline dataset database 216 comprise blood flow velocity in one embodiment, and blood pressure in other embodiments. In one embodiment, baseline dataset database 216 contains hemodynamic properties associated with survival rates of cardiac arrest subjects that received CPR. In other embodiments, baseline dataset database 216 contains hemodynamic properties associated with healthy subjects not experiencing cardiac arrest. In still other embodiments, baseline dataset database 216 comprises hemodynamic properties associated with subjective factors of a subject experiencing cardiac arrest such as age or body composition. In yet another embodiment, baseline dataset database 216 contains fluid dynamics property guidance references, such as Reynolds numbers for turbulent or laminar blood flow. One of ordinary skill in the art will envision other hemodynamic properties to include in baseline dataset database 216.

In another embodiment, baseline dataset database 216 is coupled to guidance module 212. In one embodiment, guidance module 212 is further coupled to data module 210. In such an embodiment, guidance module 212 compares a waveform of at least one measured hemodynamic property 202 to an associated hemodynamic property provided by baseline dataset database 216. The differences between at least one measured hemodynamic property 202 in data module 210 and the baseline dataset are analyzed and a corrective adjustment to CPR is calculated to produce resuscitation guidance information 240. Analysis and creation of a corrective adjustment is detailed further below in discussion of FIG. 4.

In another embodiment, blood flow monitoring device 130 comprises an electrical signal detection module 214.

Electrical detection signal module 214 is coupled to an electrical depolarization probe, such as an electrocardiogram node, to detect circulatory signals of a subject experiencing cardiac arrest, such as spontaneous resumption of cardiac activity during resuscitation. In one embodiment, electrical signal detection module 214 is coupled to guidance module 212. Guidance module 212 in such embodiments analyzes the strength of cardiac activity provided by electrical signal detection module 214, if the strength of the detected cardiac activity is sufficient to maintain survival rates of cardiac arrest as indicated by the baseline dataset provided by baseline dataset database 216, guidance module 212 issues resuscitation guidance information 240 to cease CPR. In other embodiments, if the strength of the detected cardiac activity is not sufficient to maintain survival rates of cardiac arrest as indicated by the baseline dataset provided by baseline dataset database 216, guidance module 212 issues corrective adjustments to CPR in resuscitation guidance information 240 to modify any administered CPR to maintain survival rates or mitigate post-arrest conditions in the presence of spontaneous cardiac activity detected by electrical signal detection module 214.

In one embodiment, blood flow monitoring device 130 comprises an output module 220. Output module 220 may be a graphic user interface, an audio output system, or other output means sufficient to display resuscitation guidance information 240 in accordance with various embodiments. In one embodiment, output module 220 is coupled to guidance module 212; in other embodiments, guidance module 212 comprises output module 220.

In another embodiment, blood flow monitoring device 130 comprises storage module 222. Storage module 222 in one embodiment stores the at least one measured hemodynamic property 202 collected by data module 210. Storage of such information permits future analysis of the at least one hemodynamic property 202 for survival rates or post-arrest conditions of a subject experiencing cardiac arrest and receiving CPR. In another embodiment, storage module 222 stores the resuscitation guidance information 240 issues by guidance module 212. Storage of such information permits future analysis of the resuscitation guidance information 240 for survival rates or post-arrest conditions of a subject experiencing cardiac arrest and receiving CPR. In one embodiment, storage module 222 updates baseline dataset database 216 with the hemodynamic properties and resuscitation guidance information 240 associated with survival of cardiac arrest or mitigation of post-arrest conditions of a subject.

In one embodiment, the components of vessel blow flow controller 130 are connected by a bus system 230. In another embodiment, the components of blood flow monitoring device 130 are connected by a network, accessed by network connectivity module 218. In other embodiments, network connectivity module 218 further enables wireless connection to additional devices, such as measuring probe 110 discussed previously. Additionally, in other embodiments, network connectivity module 218 permits connection of the components of blood flow monitoring device 130 across several platforms, though FIG. 2 represents the components residing in a single platform.

In one embodiment, network connectivity module 218 enables third party access to the information within blood flow monitoring device 130 in real time; for example, a health care provider could monitor the at least one hemodynamic property 202 collected in data module 210 or resuscitation guidance information 240 to provide additional feedback, or prepare follow on care responsive to the information provided. Network connectivity module 218 further permits displaying or interacting with the information of the various components of blood flow monitoring device across multiple platforms. For example, the at least one hemodynamic property 202 can be collected on data module 210 on one device and guidance module 212 can analyze the at least one hemodynamic property 202 from a separate platform. Suitable platforms, according to various embodiments, may include mobile devices such as smart phone or tablet computers, or desktop computers.

Figure 3A:
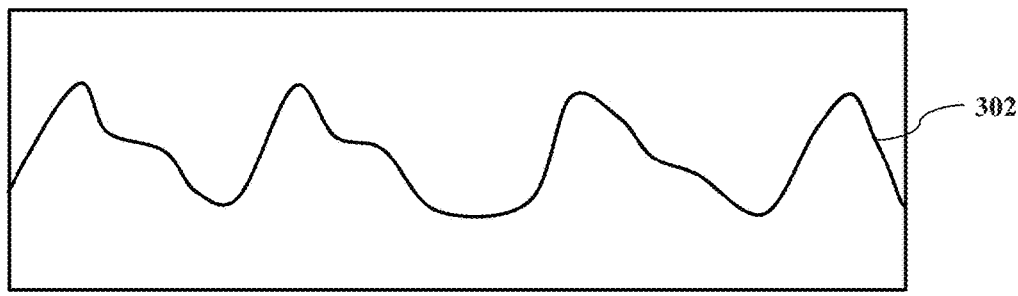
FIGS. 3A-3D illustrate a baseline dataset of a hemodynamic property and a measured hemodynamic property, both represented by waveform patterns, and waveform pattern analyses of differences between the baseline dataset hemodynamic property and the measured hemodynamic property according to embodiments of the present invention.
Figure 3B:
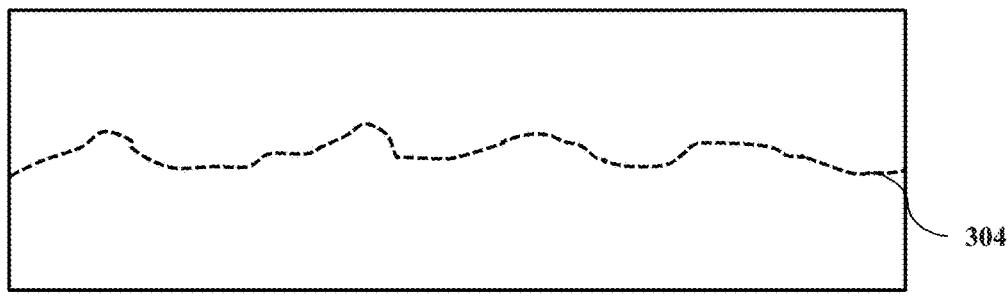

FIG. 3A illustrates a baseline dataset 302 of at least one hemodynamic property. As described previously, such baseline dataset may be derived from a subject not experiencing cardiac arrest or hemodynamic properties associated with survival rates of cardiac arrest according to various embodiments. FIG. 3B illustrates a waveform 304 of at least one hemodynamic property of a subject experiencing cardiac arrest and receiving CPR.

Figure 3C:
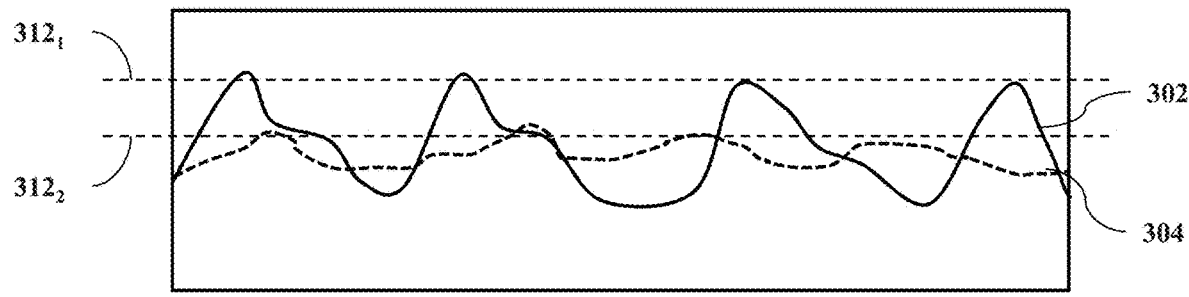
Figure 3D:
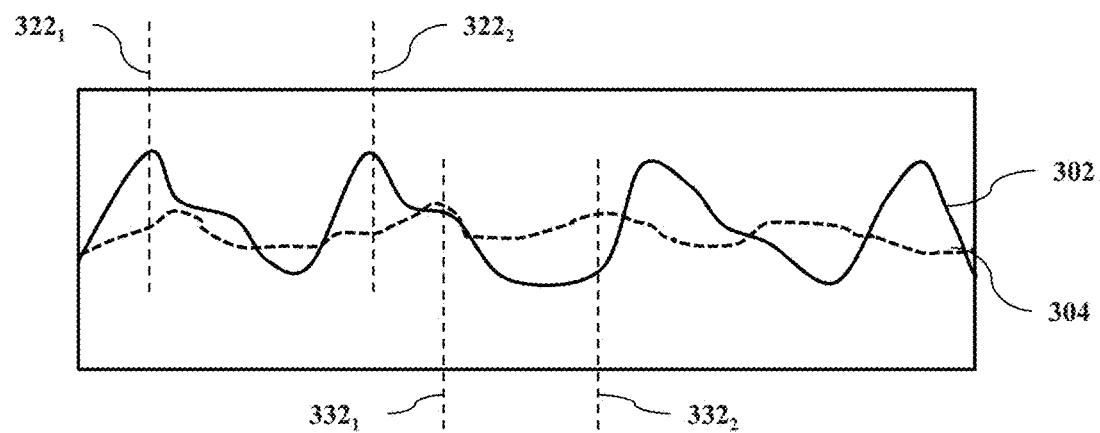

FIG. 3C illustrates an overlapping comparison of a baseline dataset 302 and waveform 304. In one embodiment, such comparison occurs in a guidance module such as guidance module 212 as described above in conjunction with FIG. 2. In one embodiment, the comparison analyzes the differences between the peak amplitude $312_1$ of baseline dataset 302 and the peak amplitude $312_2$ of waveform 304. In another embodiment, as illustrated by FIG. 3D, comparison by a guidance module analyzes a first time $322_1$ of a first peak amplitude and a second time $322_2$ of a second peak amplitude of baseline dataset 302. The guidance module further analyzes a third time $332_1$ of a third peak amplitude and a fourth time $332_2$ of waveform 304. Analysis of first time $322_1$, second time $322_2$, third time $332_1$, and fourth time $332_2$ enables the guidance module to determine the frequency of amplitudes of the baseline dataset 302 and waveform 304. One of ordinary skill in the art can envision other comparative analyses between baseline dataset 302 and waveform 304, such as the comparative areas under the curve of baseline dataset 302 and waveform 304. Comparative analysis between baseline dataset 302 and waveform 304 enables corrective adjustment calculations to produce resuscitation guidance information as described in further detail below.

Figure 4:
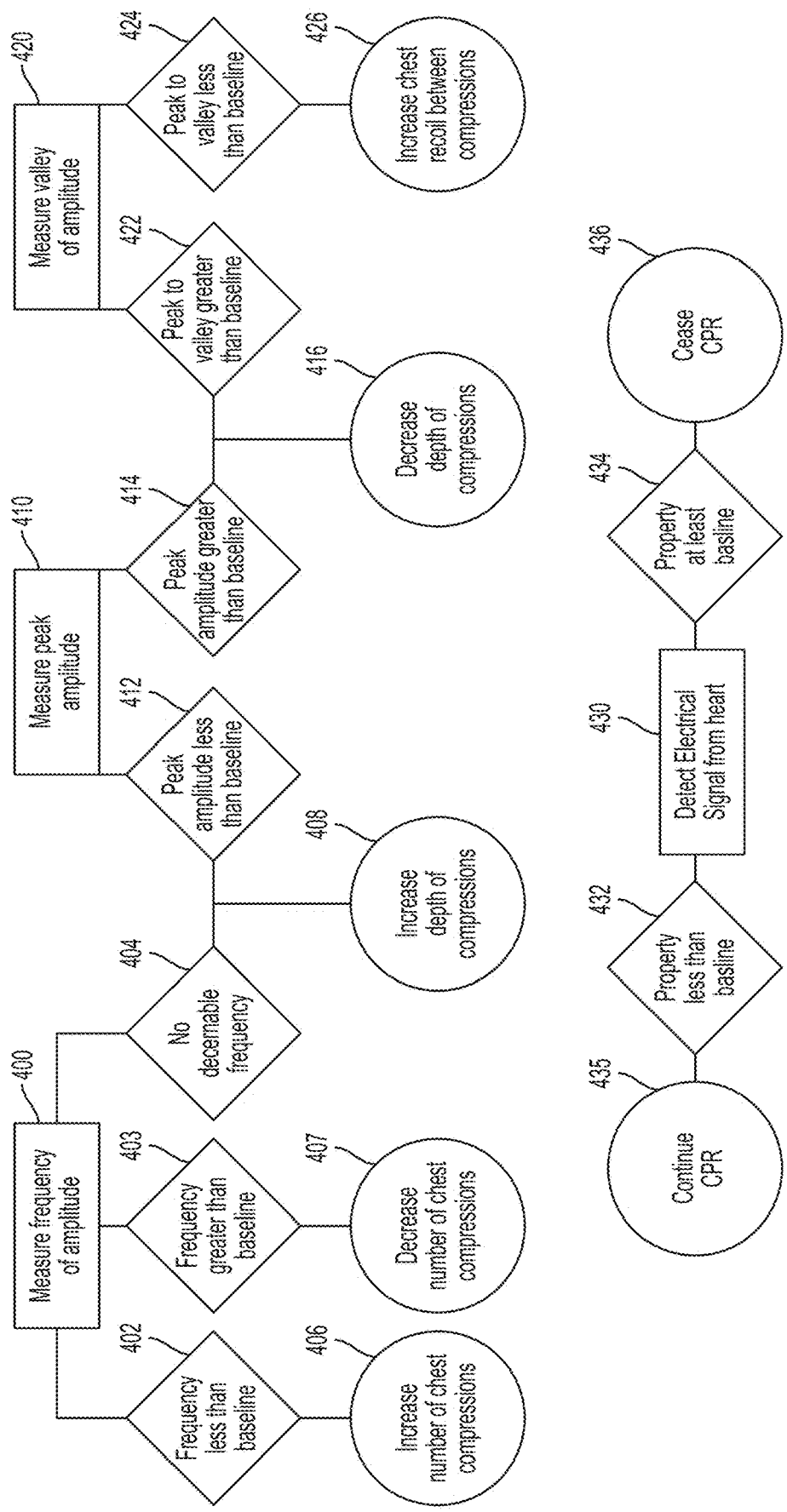
FIG. 4 illustrates a logic diagram for producing resuscitation guidance information in relation between measured hemodynamic properties and a baseline dataset according to embodiments of the present invention.

FIG. 4 illustrates a logic diagram performed by a guidance module to determine corrective adjustments to CPR for producing resuscitation guidance information. In one embodiment, the frequency of amplitude of at least one hemodynamic property of a subject experiencing cardiac arrest and receiving CPR is measured at 400. The measured frequency is compared to a baseline dataset frequency of amplitudes. In one embodiment, at 402 if the measured frequency is less than the baseline frequency the guidance module issues a corrective adjustment 406 to increase the number of chest compressions of administered CPR. In one embodiment, at 403 if the measured frequency is greater than the baseline frequency the guidance module issues a corrective adjustment 407 to decrease the number of chest compressions of administered CPR. In another embodiment, if no frequency can be determined at 404, such as by insufficient depth of chest compressions to measure the amplitudes of the waveform of the at least one hemodynamic property, the guidance module issues a corrective adjustment 408 to increase the depth of chest compressions administered by CPR.

In another embodiment, the peak amplitude of at least one hemodynamic property of a subject experiencing cardiac arrest and receiving CPR is measured at 410. The measured peak amplitude is compared to a baseline dataset peak amplitude. In one embodiment, at 412 if the measured peak amplitude is less than the baseline peak amplitude, the guidance module issues a corrective adjustment 408 to increase the depth of chest compression of administered CPR. In one embodiment, at 414 if the measured peak amplitude is greater than the baseline peak amplitude, the guidance module issues a corrective adjustment 416 to decrease the depth of chest compressions of administered CPR.

In another embodiment, the distance between the peak and valley of the amplitude of at least one hemodynamic property of a subject experiencing cardiac arrest and receiving CPR is measured at 420. The measured peak-to-valley distance of amplitude is compared to a baseline dataset of peak-to-valley distance of amplitude. In one embodiment, at 422 if the measured peak-to-valley distance of amplitude is greater than the baseline peak-to-valley distance of amplitude, the guidance module issues a corrective adjustment 416 to decrease the depth of chest compression of administered CPR. In one embodiment, at 424 if the measured peak-to-valley distance of amplitude is less than the baseline peak-to-valley distance of amplitude, the guidance module issues a corrective adjustment 426 to increase the depth of chest compressions of administered CPR. Other corrective adjustments, such as to increase the chest recoil between chest compressions, may be made to optimize blood flow as measured by a measuring probe according to alternative embodiments.

In embodiments comprising an electrical depolarization probe to detect cardiac activity such as spontaneous resumption of the heart of a subject experiencing cardiac arrest and receiving CPR, detection of such electrical signals occurs at 430. According to various embodiments, the corrective adjustments to produce resuscitation guidance information in the presence of cardiac activity detected by an electrical depolarization probe conforms to the logic processes as described above. For example, at 432, if the measured hemodynamic property resulting from spontaneous resumption of cardiac activity is less than the property of a baseline dataset, the guidance module issues a command to continue CPR at 435. According to various embodiments, the specific corrective adjustments follow the logic patterns of 400, 410, and 420 as described more fully above. In other embodiments, the property of the measured hemodynamic is at least as great as a baseline dataset at 434 and the guidance module issues resuscitation guidance information 436 to cease administered CPR.

Figure 5:
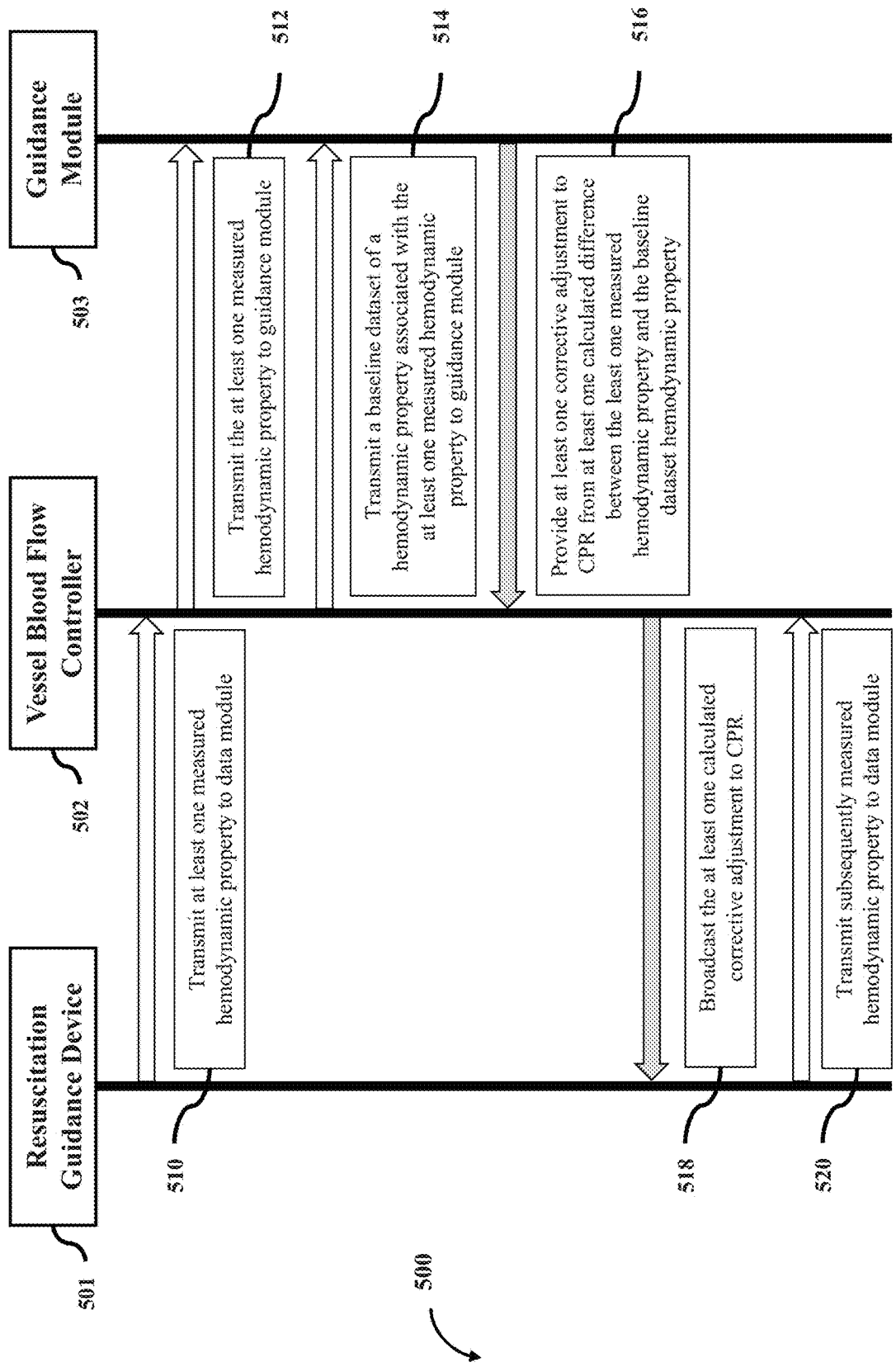
FIG. 5 illustrates a sequence diagram of a resuscitation guidance device communicating internally with a blood flow monitoring device and a guidance module by transmitting a measured hemodynamic property to the blood flow monitoring device, the blood flow monitoring device forwarding the measured hemodynamic properties with a baseline dataset associated with the measured hemodynamic property to the guidance module, and the guidance module providing a corrective adjustment for CPR as calculated from the differences between the measured hemodynamic property and baseline dataset to the blood flow monitoring device, the blood flow monitoring device broadcasting the calculated corrective adjustment, and the resuscitation guidance device transmitting a resultant hemodynamic property to the blood flow monitoring device to iteratively continue the sequence according to one or more embodiments of the present invention.

FIG. 5 illustrates a sequence diagram 500 of interaction of components according to certain embodiments of the present invention. In one embodiment, a resuscitation guidance device 501 measures at least one hemodynamic property of a subject experiencing cardiac arrest and receiving CPR. At 510, resuscitation guidance device 501 transmits the at least one measured hemodynamic property to a data module of a blood flow monitoring device 502. At 512, blood flow monitoring device 502 transmits the at least one measured hemodynamic property to a guidance module 503. In one embodiment, blood flow monitoring device 502 additionally forwards to guidance module 503 at 514 a baseline dataset for a hemodynamic property associated with the at least one measured hemodynamic property. At 516, the guidance module 503 provides the blood flow monitoring device at least one corrective adjustment to the administered CPR as calculated from analyzing the differences between the at least one measured hemodynamic property and the associated hemodynamic property of the baseline dataset. At 518 the blood flow monitoring device 502 broadcasts the corrective adjustment, such as by visual display on a graphic user interface or by audio command, to resuscitation guidance device 501. The resuscitation guidance device 501 measures a resultant hemodynamic property and at 520 transmits such a subsequently measured resultant hemodynamic property to the data module of the blood flow monitoring device 502 to begin a new iteration of sequences of analyses and corrective adjustments according to sequence 500.

It should be appreciated that the specific steps illustrated in FIG. 5 provide a particular sequence of interaction between a resuscitation guidance device 501, blood flow monitoring device 502, and guidance module 503. Other sequences of steps may also be performed according to alternative embodiments. For example, alternative embodiments of the present invention may perform the sequences outlined above in a different order. Moreover, the individual sequence illustrated in FIG. 5 may include multiple subsequences as appropriate to the individual sequence, or direct sequences between different nodes than as illustrated. Furthermore, additional sequences and exchanges may be added, or certain sequences and exchanges may be removed, depending on the particular applications. One of ordinary skill in the art would recognize many variations, modifications, and alternatives.

FIG. 6A illustrates an exemplary process 600 for providing resuscitation guidance for a subject experiencing cardiac arrest and receiving CPR. Process 600 begins at 605 by providing a baseline dataset of at least one hemodynamic property. In one embodiment, the baseline dataset is a globally desired target of the hemodynamic property, such as a hemodynamic property of a subject not experiencing cardiac arrest. In other embodiments the baseline dataset is a minimum hemodynamic property associated with survival of cardiac arrest. At 610, at least one hemodynamic property of a subject experiencing cardiac arrest and receiving CPR is measured, such as by an ultrasonic transducer in one embodiment or by infrared spectroscopy in other embodiments or bidirectional sensors in other embodiments. In some embodiments, multiple transducers or sensors measure the at least one hemodynamic property. Measured hemodynamic properties likewise vary according to the embodiment; in one embodiment blood flow velocity is measured, in another embodiment volume flow rate of blood in the subject's blood vessel is measured.

At 615, the differences between the baseline dataset of the at least one hemodynamic property and the measured at least one hemodynamic property is analyzed. At 620 a corrective adjustment to CPR is determined to manipulate the measured at least one hemodynamic property towards the baseline hemodynamic property. Determination of corrective adjustments is disclosed in further detail throughout this disclosure; in one embodiment, the corrective adjustment is to increase the depth of chest compressions. In another embodiment, the corrective adjustment is to increase the frequency of chest compressions. Other adjustments are possible in accordance with descriptions of this disclosure. At 625, the corrective adjustment is broadcast. Broadcast of the corrective adjustment varies according to embodiments of the present invention, such as by display on a graphic user interface or by audio command.

FIG. 6B illustrates an exemplary process 630 for providing resuscitation guidance for a subject experiencing cardiac arrest and receiving CPR in the presence of spontaneous circulatory activity. Process 630 begins at 635 by monitoring the electrical signals of the circulatory system of a subject experiencing cardiac arrest and receiving CPR. In one embodiment, monitoring is by an electrocardiogram node; in other embodiments, pulse detection nodes determine the presence of circulatory activity. At 640, spontaneous resumption of cardiac activity of the subject is detected. At 645, the effect of the spontaneous resumption of cardiac activity on at least one hemodynamic property of the subject is analyzed. Analysis in one embodiment is by a guidance module comparing at least one measured hemodynamic property in the presence of the detected cardiac activity with a baseline dataset of an associated hemodynamic property.

At 650, at least one corrective adjustment to the administered CPR is determined to manipulate the at least one measured hemodynamic property towards the associated hemodynamic property of a baseline dataset. In one embodiment, the corrective adjustment is to continue CPR, but modify the administration of CPR such as by intermittently compressing the chest or by slightly compressing the chest to maintain beneficial hemodynamic properties of the subject in the presence of spontaneous resumption of cardiac activity. In other embodiments, the corrective adjustment is a cessation of administered CPR. Specific corrective adjustments are described in fuller detail in discussion of FIG. 4 of this disclosure. At 655 the corrective adjustment is broadcast in ways similar to disclosure of embodiments of step 625 as discussed in describing process 600 above.

While the invention has been described in terms of particular embodiments and illustrative figures, those of ordinary skill in the art will recognize that the invention is not limited to the embodiments or figures described. For example, in various embodiments described above, a guidance module determines a corrective adjustment and delivers the corrective adjustment to an output module to display the corrective adjustment as resuscitation guidance information. However, in other embodiments, the guidance module directly displays the resuscitation guidance information. As another example, in various embodiments described above, the measuring probe and interface element are separate components. However, in other embodiments, the interface element comprises the measuring probe such that the two operations of each are performed by a single component.

Reference throughout this document to "one embodiment," "certain embodiments," "an embodiment," or similar term means that a particular feature, structure, or characteristic described in connection with the embodiment is included in at least one embodiment. Thus, the appearances of such phrases in various places throughout this specification are not necessarily all referring to the same embodiment. Furthermore, the particular features, structures, or characteristics may be combined in any suitable manner on one or more embodiments without limitation.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." The term "or" as used herein is to be interpreted as inclusive or meaning any one or any combination. Therefore, "A, B or C" means any of the following: A; B; C; A and B; A and C; B and C; A, B and C. An exception to this definition will occur only when a combination of elements, functions, steps or acts are in some way inherently mutually exclusive.

Words using the singular or plural number also include the plural and singular number, respectively. Additionally, the words "herein," "above," and "below" and words of similar import, when used in this disclosure, shall refer to this disclosure as a whole and not to any particular portions of the disclosure.

The description of embodiments of the disclosure is not intended to be exhaustive or to limit the disclosure to the precise form disclosed. While specific embodiments and examples for the disclosure are described herein for illustrative purposes, various equivalent modifications are possible within the scope of the disclosure, as those skilled in the relevant art will recognize. Such modifications may include, but are not limited to, changes in the dimensions and/or the materials shown in the disclosed embodiments.

All of the references cited herein are incorporated by reference. Aspects of the disclosure can be modified, if necessary, to employ the systems, functions, and concepts of the above references to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A cardiac arrest resuscitation guidance medical device, comprising:
a measuring probe capable of measuring at least one hemodynamic property of blood flowing through at least one blood vessel of a subject, wherein the at least one hemodynamic property includes blood flow in a first direction and blood flow in a second direction;
an interface element coupled to the measuring probe, wherein a first side of the interface element comprises reference indicia guiding application of the interface element along a sternocleidomastoid of the subject and reference indicia guiding application of the interface element along a jawline of the subject, wherein a second side of the interface element comprises an adhesive material for adhering the interface element to the subject, and wherein the interface element includes a mechanical fixture to angle a face of the measuring probe with respect to the at least one blood vessel; and a blood flow monitoring device operably coupled to the measuring probe, the blood flow monitoring device comprising: at least one processor effective to execute instructions that cause the at least one processor to:

collect data representing at least one measured hemodynamic property of the blood, the at least one measured hemodynamic property of the blood including blood flow in a first direction and blood flow in a second direction;

determine a net hemodynamic property of the blood based on the blood flow in the first direction and the blood flow in the second direction; and display resuscitation guidance information describing at least one action capable of correctively adjusting the net hemodynamic property of the blood.

2. The medical device of claim 1, wherein the measuring probe includes an ultrasonic transducer.

3. The medical device of claim 1, wherein the measuring probe measures blood pressure of the subject.

4. The medical device of claim 1, wherein the at least one blood vessel of the subject includes a carotid artery.

5. The medical device of claim 1, wherein the adhesive material comprises a hydrogel capable of propagating acoustic signals from the measuring probe to the at least one blood vessel of the subject.

6. The medical device of claim 1, further comprising an electrical depolarization probe coupled to the blood flow monitoring device to detect electrical signals of a circulatory system.

7. The medical device of claim 1, wherein the blood flow monitoring device further comprises a baseline dataset accessible by the at least one processor.

8. The medical device of claim 7, wherein the resuscitation guidance information displayed by the at least one processor comprises a corrective adjustment responsive to a requirement of the baseline dataset.

9. The medical device of claim 8, wherein the corrective adjustment is a command to increase a depth of chest compressions applied by cardiopulmonary resuscitation.

10. The medical device of claim 1, further comprising an electrical depolarization probe configured in communication with the at least one processor, the electrical depolarization probe capable of detecting electrical signals of a circulatory system.

11. The medical device of claim 10, wherein the corrective adjustment is a command to cease cardiopulmonary resuscitation upon detecting electrical signals from the electrical depolarization probe, the electrical signals consistent with sufficient spontaneous circulatory activity.

12. A method of providing resuscitation guidance during cardiac arrest, the method comprising:

applying an interface element including a measuring probe to a subject according to reference indicia on a first side of the interface element, wherein the reference indicia guide application of the interface element along a sternocleidomastoid of the subject and along a jawline of the subject;

providing a minimum baseline dataset of at least one hemodynamic property, wherein the minimum baseline dataset includes a baseline cerebral perfusion waveform;

measuring at least one hemodynamic property, wherein the at least one hemodynamic property includes a blood flow in a first direction and a blood flow in a second direction;

determining a waveform that represents cerebral perfusion based on the blood flow in the first direction and the blood flow in the second direction;

comparing at least one of an amplitude and a frequency of the waveform to at least one of an amplitude and a frequency of the baseline cerebral perfusion waveform to determine at least one corrective adjustment to manipulate the at least one measured hemodynamic property towards the at least one hemodynamic property of the minimum baseline dataset; and providing the at least one corrective adjustment.

13. The method of claim 12, wherein the measuring of the at least one hemodynamic property is performed by at least one ultrasonic transducer.

14. The method of claim 12, wherein the at least one hemodynamic property includes blood pressure.

15. The method of claim 12, wherein the providing of the at least one corrective adjustment includes presenting the at least one corrective adjustment visually on a graphic user interface.

16. The method of claim 12, wherein providing the at least one corrective adjustment includes transmitting, to a chest compression device, a command to change a rate of chest compressions or a command to change a depth of chest compressions.

17. The method of claim 12, further comprising monitoring electrical depolarization signals of a circulatory system.

18. The method of claim 16, wherein the at least one corrective adjustment includes a command to cease administration of the at least one corrective adjustment upon detecting electrical signals from an electrical depolarization probe, the electrical signals consistent with sufficient spontaneous circulatory activity.

19. The method of claim 12, wherein comparing at least one of the amplitude and the frequency of the waveform to at least one of the amplitude and the frequency of the baseline cerebral perfusion waveform to determine at least one corrective adjustment to manipulate the at least one measured hemodynamic property towards the at least one hemodynamic property of the minimum baseline dataset comprises:

determining a frequency difference between the frequency of the waveform and the frequency of the baseline cerebral perfusion waveform; and determining a corrective adjustment to a chest compression rate based on the frequency difference.

20. The method of claim 12, wherein comparing at least one of the amplitude and the frequency of the waveform to at least one of the amplitude and the frequency of the baseline cerebral perfusion waveform to determine at least one corrective adjustment to manipulate the at least one measured hemodynamic property towards the at least one hemodynamic property of the minimum baseline dataset comprises:

determining an amplitude difference between the amplitude of the waveform and the amplitude of the baseline cerebral perfusion waveform; and determining a corrective adjustment to a chest compression depth based on the amplitude difference.

* * * * *